(12) United States Patent
Hellyer et al.

(10) Patent No.: US 7,371,531 B2
(45) Date of Patent: May 13, 2008

(54) USE OF AN EXTRACTION CONTROL IN A METHOD OF EXTRACTING NUCLEIC ACIDS

(75) Inventors: Tobin Hellyer, Westminster, MD (US); Thomas Fort, Hanover, PA (US); Ray A. McMillian, Timonium, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 150 days.

(21) Appl. No.: 11/114,952

(22) Filed: Apr. 25, 2005

(65) Prior Publication Data

US 2006/0014170 A1  Jan. 19, 2006

Related U.S. Application Data

(60) Provisional application No. 60/564,926, filed on Apr. 23, 2004.

(51) Int. Cl.
*C12Q 1/68* (2006.01)
*C07H 21/00* (2006.01)

(52) U.S. Cl. .......................... 435/6; 536/25.4
(58) Field of Classification Search .................. 435/6; 536/25.4
See application file for complete search history.

(56) References Cited

U.S. PATENT DOCUMENTS

| 5,576,178 | A | * | 11/1996 | Emanuel et al. | 435/6 |
| 5,837,501 | A | * | 11/1998 | Beumer et al. | 435/91.2 |
| 6,001,572 | A | * | 12/1999 | Toothman | 435/6 |
| 6,379,897 | B1 | * | 4/2002 | Weidenhammer et al. | 435/6 |
| 6,642,033 | B1 | * | 11/2003 | Lazo et al. | 435/91.1 |
| 6,649,378 | B1 | * | 11/2003 | Kozwich et al. | 435/91.2 |
| 6,818,762 | B2 | * | 11/2004 | Rundell et al. | 536/23.1 |
| 2002/0068821 | A1 | * | 6/2002 | Gundling | 536/23.1 |
| 2003/0108875 | A1 | * | 6/2003 | Exner et al. | 435/6 |
| 2005/0014153 | A1 | * | 1/2005 | Hlillebrand et al. | 435/6 |
| 2005/0130227 | A1 | * | 6/2005 | Yeung et al. | 435/7.1 |
| 2005/0239091 | A1 | * | 10/2005 | Collis et al. | 435/6 |
| 2005/0282170 | A1 | * | 12/2005 | Fradet et al. | 435/6 |
| 2006/0217341 | A1 | * | 9/2006 | Volkin et al. | 514/44 |
| 2007/0015139 | A1 | * | 1/2007 | Gayral et al. | 435/5 |

FOREIGN PATENT DOCUMENTS

WO  0146463 A  6/2001

OTHER PUBLICATIONS

The Stratagene Catalog p. 39(1988).*
Matthews et al. Review : Analytical Strategies for the use of DNA probes. Analytical Biochemistry 169 : 1-25 (1988).*
Tyagi et al., Molecular Beacons: Probes that fluoresce upon Hybridization. Nature Biotechnology 14 :303-308 (Mar. 1996).*
Inglis et al., A survey of Camplobacter species shed in faeces of beef cattle using polymerase chain reaction. ☐☐Canadian J. of Microbiology 49 : 655-661 (2003).*
Sunters et al., The use of alpha-DNA as an internal standard in the detection and quantification of DNA damage in specific genes using Southern blotting. Nucleic Acids Research 24(12) : 2456-2457 (1996).*
Chelly et al., Transcription of the dystrophin gene in human muscle and non-muscle tissues. Nature 333: 858-860 (1988).*
Petersen N E, et al., "Improved RNase protection assay for quantifying LDL-receptor mRNA; estimation of analytical imprecision and biological variance in peripheral blood mononuclear cells." Clinical Chemistry Nov. 1995, vol. 41, No. 11, pp. 1605-1613.
Witt D J, et al., "Techniques for the evaluation of nucleic acid amplification technology performance with specimens containing interfering substances: efficacy of boom methodology for extraction of HIV-1 RNA." Journal of Virological Methods Apr. 1999, vol. 79, No. 1, pp. 97-111.
Moody A, et al., "Measuring infectious bursal disease virus RNA in blood by multiplex real-time quantitative RT-PCR." Journal of Virological Methods, Amsterdam, NL, vol. 85, No. 1-2, Mar. 2000, pp. 55-64.
Boom R, et al., "Rapid and Simple Method for Purification of Nucleic Acids." Journal of Clinical Microbiology, Washington, DC, USA, vol. 28, No. 3, Mar. 1, 1990, pp. 495-503.
Mumy Karen L, et al., "Convenient determination of DNA extraction efficiency using an external DNA recovery standard and quantitative-competitive PCR." Journal of Microbiological Methods, May 2004, vol. 57, No. 2, pp. 259-268, XP002435441 & Database Science Direct online version of document, Mar. 14, 2004.
Petersen D G, et al., "Improvements for comparative analysis of changes in diversity of microbial communities using internal standards in PCR-DGGE." FEMS Microbiology Ecology, Elsevier, NL, vol. 53, No. 3, Aug. 1, 2005, pp. 339-348.

* cited by examiner

*Primary Examiner*—Ethan Whisenant
(74) *Attorney, Agent, or Firm*—Alan M. Kiang

(57) ABSTRACT

The present invention relates to a method of ensuring the effectiveness of the extraction workup from a biological sample of nucleic acid. The inventive method is able to distinguish between possible defects in the extraction of nucleic acid from a sample and possible defects in a subsequent amplification step. The present invention also relates to a packaged array for extracting nucleic acid from a biological sample.

18 Claims, 7 Drawing Sheets

FIGURE 1

1. Add Extraction Control (EC) to biological sample suspected of containing the target nucleic acid 2. Transfer sample to extraction vessel containing iron oxide particles (IOP)

3. Add binding acid

4. Mix and separate with magnet

5. Add wash solution

6. Mix and separate with magnet

7. Add elution buffer

8. Mix and separate with magnet

9. Assay the elution buffer for the presence of the extraction control.

Series 1 = + CT DNA, + EC, + Binding Acid
Series 2 = + CT DNA, No EC, + Binding Acid
Series 3 = No CT DNA, + EC, + Binding Acid
Series 4 = + CT DNA, + EC, No Binding Acid

USE OF AN EXTRACTION CONTROL IN A METHOD OF EXTRACTING NUCLEIC ACIDS

Priority is claimed under 35 U.S.C. § 119(e) to provisional application U.S. 60/564,926, filed Apr. 23, 2004.

FIELD OF THE INVENTION

The present invention relates to a method of determining the efficacy of an extraction step in a process for the working up of a biological sample containing a nucleic acid. The present invention also relates to a packaged array for extracting a nucleic acid from a biological sample.

DESCRIPTION OF RELATED ART

Extracting a nucleic acid from a sample is an important operation in processes in clinical diagnosis, cloning, purification and isolation and other processes in biotechnology. For instance, gene recombinant technology requires the isolation of both a vector DNA and the cloned and/or expressed DNA. In order to diagnose a genetic disease or detect a cancer gene, it is necessary to extract the desired nucleic acid from the tissue, the cells, and the various other biological materials in a sample.

A nucleic acid does not occur free in nature. It is found in bacteria, cells, or virus particles, surrounded by a cell membrane and/or cell wall composed of proteins, lipids and sugars. A nucleic acid generally forms complexes with histone and/or other proteins in its natural environment. To extract a nucleic acid, the surrounding cell membranes and cell walls must be disrupted. In the case of isolating a nucleic acid, the nucleic acid-protein complex needs to be denatured or degraded to free the desired nucleic acid from the complex so that it can be solubilized and extracted. Methods of extracting nucleic acids are described, for example, in U.S. Pat. No. 6,043,032, incorporated herein in its entirety.

Internal standards have been applied in nucleic acid analysis. These include constitutively expressed mRNAs to control for the effectiveness of the workup. Further, external controls have been applied in the extraction step in nucleic acid amplification-based analysis. However, the detection and/or quantification of the control has required amplification, so it is not possible to distinguish whether a problem in the process has arisen from the amplification step or in the extraction step. For example, in U.S. Pat. No. 6,387,652 B1, addition of *G. candidum* sequences as a reference to assays for fungal target sequences was employed as a control. However, it was necessary to assume an amplification efficiency of one (col. 19, lines 45-61).

Up to the present there has been no method of verifying the extraction process alone for a nucleic acid, independent of the downstream application, such as an amplification step.

SUMMARY OF THE INVENTION

The present invention relates to a method of determining the effectiveness of an extraction step in the workup of a sample of a target nucleic acid. The present invention further relates to a packaged array for extracting a target nucleic acid from a biological sample. In a further embodiment, the method and packaged array of the present invention can be incorporated in a robotic assembly for the automated analysis for the presence of a disease organism in a biological sample.

BRIEF DESCRIPTION OF THE DRAWINGS

FIG. 1 is a flowchart for one embodiment of an extraction protocol using an automated system for the extraction of DNA from urine and vaginal specimens on the BD Viper™ Sample Processor.

DETAILED DESCRIPTION

Figure 2:
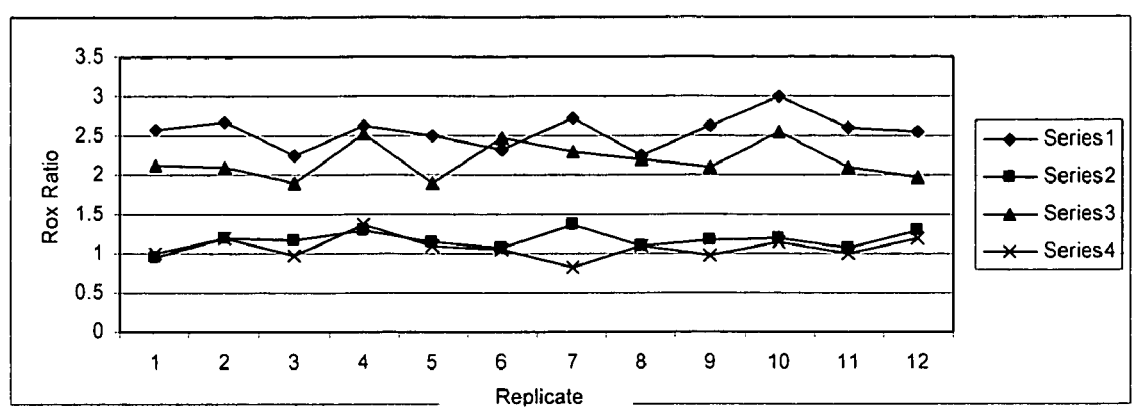
FIG. 2 is a graph of the results presented for Example 1.

The present invention relates to a method of ensuring or verifying the extraction of a target nucleic acid from a biological sample.

The target is a nucleic acid such as single or double-stranded DNA and RNA. Examples of nucleic acid that can be extracted by the method include not only genomic DNA or RNA from animals, plants, bacteria, viruses, fungi and parasitic organisms, but also the DNA or RNA of mitochondria or chloroplasts. Examples of other classes of nucleic acid that can be extracted by the method include not only mRNA, but also tRNA, rRNA, and tmRNA (transfer-messenger RNA) as well as plasmid DNA. DNA and RNA extracted by the method of the invention may also be either wholly or partially single-stranded or possess other tertiary or quaternary structure. A sample containing nucleic acids is exemplified by viable samples such as leukocyte cells, the culture of host cells containing vectors or the like that are typically prepared by gene recombinant technology, cells infected with viruses or phages, viruses in blood, and the culture of a sample microorganism. The culture may contain microorganisms but its supernatant alone is sufficient. Not only an artificial culture but also a naturally occurring culture is applicable. In case of a sample containing lumps of microorganism, homogenization or sonication may be performed as required to achieve good efficiency of extraction.

Alternative sample types include but are not limited to biological specimens for the diagnosis of infectious or non-infectious diseases, environmental specimens, or samples of food or water. The target nucleic acid may be a particular sequence or it may be a class of nucleic acid. A class of nucleic acid is, for a particular assay method, those molecules of nucleic acid whose chemical, physical or biological properties are such that they can be expected to be extracted effectively in methods used for nucleic acid extraction. Typically, but not necessarily, the nucleic acids of a class are all DNA or DNA analogs or all RNA or RNA analogs.

Targeted organisms can include but are not limited to *Chlamydia trachomatis, Neisseria gonorrhoeae*, Human Immunodeficiency Virus ½ , Hepatitis C Virus, Hepatitis B Virus, Severe Acute Respiratory Syndrome Virus, Influenza A/B, Herpes Simplex Viruses 1-6, Enteroviruses, West Nile Virus, Parainfluenza viruses, Adenoviruses, Respiratory Syncytial Virus A/B, Mycobacterium paratuberculosis, Mycobacterium avium-intracellulare complex, Mycobacterium tuberculosis complex, Cytomegalovirus, Group B Streptococcus, Bordetella pertussis, and Bordetella parapertussis.

In one aspect of the invention, the target nucleic acid is a particular RNA or cDNA from one ore more of the following sources: bacterial pathogens, bacterial non-pathogens, viral pathogens, viral non-pathogens, fungal pathogens, fungal non-pathogens, yeast pathogens, yeast non-pathogens, parasitic pathogens, parasitic non-pathogens, plants, animal products, food, total RNA or cDNA within the sample matrix, total prokaryotic RNA or cDNA, total eukaryotic RNA or cDNA, or total viral RNA or cDNA.

In another aspect of the invention, the target nucleic acid sought is DNA from one or more of the following sources: bacterial pathogens, bacterial non-pathogens, viral pathogens, viral non-pathogens, fungal pathogens, fungal non-pathogens, yeast pathogens, yeast non-pathogens, parasitic pathogens, parasitic non-pathogens, plants, animal products, food, total DNA within the sample matrix, total genomic prokaryotic DNA, total genomic eukaryotic DNA, or total viral DNA.

According to the method of the present invention, an extraction control is added to the biological sample before the extraction step. The extraction control is a nucleic acid sequence with a distinguishable label. By distinguishable label is meant a label or marker that can be identified and quantified by a radiometric, spectrometric, fluorogenic or colorimetric method in the presence of unlabeled nucleic acid and other components of the sample matrix. The use of an extraction control for the extraction process is understood as the use of a reference or standard to allow for verification that the extraction occurred as desired. Calibration and quantification of the extraction control are also possible. The extraction control is designed to be detected without amplification of its nucleotide sequence, and further designed so as not to interfere with amplification of the target nucleic acid.

Nucleic acid labels are known in the art. These include, but are not limited to, donor quencher dye pairs such as fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS). Any dye pair which produces fluorescence quenching can be used in the methods of the invention, regardless of the mechanism by which quenching occurs.

Preferred labels for extraction control include fluorophores such as fluorescein and rhodamine, radioactive labels such as $^{32}P$ or $^{35}S$, enzymes such as horseradish peroxidase, alkaline phosphatase, glucose oxidase, β-galactosidase, soybean peroxidase or luciferase. Methods for linking the detectable moieties with the nucleic acid in a form that is stable to most methods of handling nucleic acid are known in the art. For example, methods for making covalent linkages are provided commercially by companies such as Integrated DNA Technologies (see IDT technical bulletins, available via the internet at the Integrated DNA Technologies website). Other labeling methods include having the detectable moiety attached to one member of a highly stable binding pair, and the other member of the binding pair attached to the nucleic acid. Such a binding pair can be, for example, avidin (or streptavidin) and biotin. Avidin-biotin labeling techniques are described for example in *Advances in Biomagnetic Separation* (M. Uhlen, E. Hornse, and O. Olsvik) (Eds.), Eaton Publishing 1994).

The nucleotide sequence of the extraction control must be sufficiently long to have the general physical and chemical properties of nucleic acid. In one embodiment, the extraction control consists essentially of a nucleotide sequence between 21 and 61 bases in length and a label. In another embodiment, the nucleotide sequence, labeled with for example rhodamine, must be sufficiently long to reversibly bind to an iron oxide particle under extraction conditions such as described in U.S. Pat. No. 6,433,160, where free rhodamine does not bind to an iron oxide particle.

The extraction control can be added to a biological sample before or after lysis/disruption of the cell membrane or cell wall. In certain circumstances, such as with an RNA-based extraction control that is susceptible to degradation by RNAses, the extraction control should not be added until the point immediately before extraction. For procedures involving binding of nucleic acid to a solid support, the extraction control generally may be added at any point prior to the binding, and thereby control for all subsequent phases of the process.

Following addition of an extraction control, the step of extracting nucleic acid is performed. The phrase "extracting nucleic acid" refers to purifying nucleic acid sufficiently away from protein or other material within the sample matrix so that it has purity reasonably sufficient for assays to identify or quantify segments of nucleic acid. The term "protein" is used to include chains of amino acids or amino acid derivatives comprising peptides, polypeptides or full-length proteins. Methods of extracting nucleic acids are known in the art. For example, U.S. Pat. No. 6,043,032 describes several methods of extracting nucleic acid, including liquid phase extraction methods, incorporated herein in its entirety.

The extraction procedure can include a step in which the nucleic acid is bound to a solid support. The solid support is typically washed to remove undesired material. In many instances, the nucleic acid is released from the solid support and processed further. In other instances, the nucleic acid bound to the solid support is processed further. Those of skill will recognize when it is appropriate to assess extraction as opposed to assessing a subsequent procedure. Often, the assessment is made after release from the solid support. Or, if no such release is required, the assessment can be made of the nucleic acid bound to the support. Appropriate supports for non-specific capture of nucleic acids include, but are not limited to, crushed glass powders (e.g., available from Bio101 as GeneClean®) and glass fiber filters (e.g., available from Roche as the High Pure™ system, Celite (e.g., available from BioRad Laboratories as Prep-A-Gene™), and iron-containing paramagnetic particles (e.g., as described in U.S. Pat. No. 6,433,160, which discloses nucleic acid binding under acidic conditions). For target-specific capture, paramagnetic particles with modified surfaces may be used (e.g., such as described in European Specification EP 0 446 260 B1 and U.S. Pat. No. 5,512,439, with each particle carrying a plurality of molecules of an oligonucleotide). The captured oligonucleotides may be conjugated directly to the particle surface or coupled via an intermediary linker such as a streptavidin-biotin or other receptor-ligand interaction, as is known in the art.

Following extraction to yield an extract containing the extraction control and the target nucleic acid, the presence of the extraction control in the extract is verified by detection of the label, also known as a detectable marker. The extraction control label can be further analyzed by the detection method to allow for quantification of the amount of extraction control in the extract. Suitable methods for detection of the label include radiometric, spectrometric, fluorogenic or colorimetric methods.

The extraction control can have a detectable marker whose detection characteristics (e.g., emission or absorption wavelengths) overlap the detection characteristics that will be utilized in a post-extraction procedure, such as an assay for a specific molecule. For example, the chromophores or fluorophors used for the extraction control and in the second post-extraction procedure can be the same. In such case, the detection of the extraction control and the detection in the subsequent procedure are designed so that a positive extraction yields an amount of detectable marker that will, in the subsequent procedure, contribute only an amount of signal to the result as can be reliably compensated for in a controlled-for background signal.

The data from detection of the labeled extraction control is optionally normalized. The step of normalizing data can comprise interpolating from the control data how much any experimental data point should be normalized or can comprise discarding data points that the control data indicates is unreliable or which may be considered as background signal. The detection and normalization of data can be combined in a single step for purposes of automation.

In one embodiment, the nucleic acid sequence of the extraction control is substantially based on the structure of the target nucleic acid. Thus, for example, the method can seek to extract a given structural gene, open reading frame (ORF), intron, exon, mRNA, cDNA, and the nucleic acid of the extraction control can be designed to contain 1% or more, 10% or more, or 50% or more of the primary structure of the same. Thus, in one embodiment, if RNA is sought to be extracted, the extraction control will be RNA (or an RNA analog), and if DNA is sought to be extracted the extraction control will be DNA (or a DNA analog). In other embodiments, if RNA is to extracted, the extraction control may be DNA (or a DNA analog) and if DNA is to be extracted, the extraction control may be RNA (or an RNA analog).

A structural gene is defined by the nucleic acid segment (and if relevant its complement) that codes for a transcribed RNA (whether such RNA is later edited to remove introns or the like) or that codes for the minimum contiguous segment that codes for an expressed protein. Given the existence of splice variants, and the typical existence of RNA at the 5' and 3' ends of mRNA that is not translated into protein, a given gene may define one, two or several structural genes. In all cases, the presence of a modification with a label of a residue or nucleotide, which would otherwise comprise shared sequence, does not diminish the shared percentage. For recitations of percent identical structure, if the percentage required exists for at least one of the structural genes, then the recitation is satisfied.

In another embodiment, if two or more target nucleic acids with different characteristics are to be extracted, two or more extraction controls may be added before the extraction step.

If the target nucleic acid to be extracted has features that are associated with difficulties in extraction, these features may be modeled in the substances selected as the extraction controls. For example, if a particular nucleic acid segment is sought, and that segment includes a high G/C content segment, or a high degree of secondary or tertiary structure that contributes to the difficulty of extracting the desired segment, then such sub-segment or a homolog thereof may be included in the sequence of the extraction control. The design of the extraction control also includes the limitation that the extraction control should not interfere with post-extraction amplification of the target sequence.

In many contexts for extracting nucleic acid, a hybridization reaction will be used in a post-extraction procedure. For many such post-extraction procedures, the use of nucleic acids for the extraction control with a sequence based on an intron sequence will minimize undesired competing hybridizations. Internal hairpin structures can also minimize undesired competing hybridizations. Where polymerase-based methods are used in post-extraction procedures, the 3' end of the extraction control can be modified to prevent extension of the extraction control. For example, the detectable marker can be attached to the 3' end to block extension or the 3' end of the extraction control may be capped using a dideoxynucleotide, inverted base or other non-extendable terminal moiety as is known in the art. Other methods of inhibiting undesired amplification are known in the art, for example in U.S. Pat. No. 5,972,610 and U.S. Pat. No. 5,849,497. Determining whether or not an extraction control will interfere with amplification of the target sequence can be accomplished by running in parallel an amplification of the target sequence with and without the extraction control.

A distinction is made between nucleic acid amplification and signal amplification. By nucleic acid amplification is meant a technique such as SDA, PCR, TMA, NASBA, etc., whereby additional copies of the nucleic acid are made. In contrast, signal amplification such as that which occurs with a chemiluminescent or calorimetric label is used in the detection of a label, and does not result in additional copies of the label. The use of the general term "amplification" in reference to post-extraction amplification is meant to refer to nucleic acid amplification. An extraction control sequence is defined as not capable of being amplified during post-extraction amplification if, at the conclusion of amplifying the target sequence, the amount of extraction control sequence present in the reaction mixture is less than 1000-fold more than was present prior to amplification. The extraction control of the present invention is designed to not participate in or interfere with a subsequent amplification step of the target nucleic acid, including amplification of sequences added to independently measure or control for the efficiency of the amplification step. Non-participation or non-interference by the extraction control is defined by running parallel amplifications of the target sequence with and without the extraction control. If the amplification of the target sequence in the presence of the extraction control is roughly equivalent to the amplification of the target sequence without the extraction control, then the extraction control is defined as not participating, or not interfering with, the post-extraction amplification of the target sequence.

In one embodiment of the invention, multiple extraction controls are included in the extraction procedure, each designed specifically to verify the extraction of one or more classes of nucleic acid. In another embodiment of the invention, the extraction control can be dried for long-term storage without impacting its form or function.

FIG. 1 contains a general flowchart for an extraction protocol using an automated system for the extraction of DNA from urine and vaginal specimens on the BD Viper™ Sample Processor, which is an example of a packaged array. The following examples further illustrate the present invention, but of course, should not be construed as in any way limiting its scope.

EXAMPLE 1

An experiment was conducted to evaluate the ability of a Rhodamine (ROX) labeled extraction control to detect automated nucleic acid extraction failures. The control was designated BBTEC-26 (SEQUENCE ID NO. 1). The protocol was as follows:

Spike pooled male and female urine with 7500 copies of *Chlamydia trachomatis* (CT) plasmid per mL. (Each plasmid carried a single copy of the amplification target sequence.)

Heat spiked or unspiked (control) urine samples at 114° C. for 30 minutes.

Transfer urine to extraction tubes containing 40 mg ferrosoferric oxide ($Fe_3O_4$).

Transfer 111 picomoles of BBTEC-26 Extraction Control (EC) to the desired tubes.

Extract on the BD Viper™ (extraction-equipped breadboard instrument) using the following automated protocol:

Add 50 μL binding acid to the extraction tubes and mix. (Binding acid solution facilitates nucleic acid binding to ferrosoferric oxides as is described in U.S. Pat. No. 5,973,138) Omit binding acid from control tubes. The binding acid was 5M phosphoric acid ($H_3PO_4$).

Position magnets next to extraction tubes to lock $Fe_3O_4$ and any bound nucleic acid to sides of tubes.

Aspirate unbound sample from the extraction tubes and transfer to waste.

Transfer 1030 μL wash buffer to each extraction tube and mix. Wash buffer was 1 mM glycine-HCl.

Position magnets next to extraction tubes to lock $Fe_3O_4$ and bound nucleic acid to sides of tubes.

Aspirate unbound solution from the extraction tubes and transfer to waste.

Transfer 370 μL elution buffer to each extraction tube and mix. The elution buffer has a basic pH. The elution buffer was 177.8 mM Bicine, 88.3 mM KOH, 11% DMSO, and 12.1% glycerol.

Position magnets next to extraction tubes to lock $Fe_3O_4$ to sides of tubes.

Aspirate eluate from the extraction tubes and transfer to BD ProbeTec™ ET CT Amplified DNA Assay.

Collect, normalize and average ROX signals from passes 20-60 of the incubation in the BD ProbeTec™ ET instrument to assess EC extraction adequacy.

Collect BD ProbeTec CT assay results (MOTA scores, corresponding to the area under the amplification curve) to assess the adequacy of CT target recovery and amplification.

The data below are presented in MOTA values for the CT determinations and in machine-normalized ROX values for the EC determinations. Free ROX dye will not bind to ferric oxide under the conditions used for the extraction. The MOTA values represent the sum of individual fluorescence measurements over time using a fluorometer with an established cutoff level for a positive reaction of 2,000 for the BD ProbeTec™ ET CT and GC Amplified DNA Assays. BD ProbeTec™ brand assay kits are available from Becton, Dickinson and Company, and are designed for use with use the BD ProbeTec™ ET System for Strand Displacement Amplification (SDA). The BD Viper™ Sample Processor automates the sample handling associated with high-volume testing using the BD ProbeTec™ ET System.

Results

| Tube | Target MOTA 1 | Target MOTA 2 | EC Score (ROX Assay Well/ROX Normalizer) 1 | EC Score (ROX Assay Well/ROX Normalizer) 3 | Target MOTA 1 | Target MOTA 2 | EC Score (ROX Assay Well/ROX Normalizer) 1 | EC Score (ROX Assay Well/ROX Normalizer) 2 |
|---|---|---|---|---|---|---|---|---|
| | +CT +EC +Binding Acid | | | | +CT No EC +Binding Acid | | | |
| 1 | 82765 | 81900 | 2.57 | 2.72 | 64083 | 107523 | 0.95 | 1.38 |
| 2 | 89858 | 72722 | 2.68 | 2.25 | 57317 | 62082 | 1.19 | 1.11 |
| 3 | 61719 | 92915 | 2.24 | 2.62 | 80405 | 82031 | 1.18 | 1.18 |
| 4 | 83622 | 96592 | 2.63 | 3.00 | 73549 | 75247 | 1.31 | 1.19 |
| 5 | 55736 | 89618 | 2.49 | 2.31 | 82858 | 84116 | 1.15 | 1.07 |
| 6 | 47094 | 48845 | 2.32 | 2.55 | 45150 | 95490 | 1.07 | 1.31 |
| | No CT +EC +Binding Acid | | | | +CT +EC No Binding Acid | | | |
| 1 | 0 | 3 | 2.12 | 2.31 | 2367 | 7876 | 0.99 | 0.83 |
| 2 | 0 | 0 | 2.11 | 2.20 | 63027 | 4 | 1.19 | 1.09 |

-continued

| | Target MOTA | | EC Score (ROX Assay Well/ROX Normalizer) | | Target MOTA | | EC Score (ROX Assay Well/ROX Normalizer) | |
|---|---|---|---|---|---|---|---|---|
| Tube | 1 | 2 | 1 | 3 | 1 | 2 | 1 | 2 |
| 3 | 0 | 0 | 1.89 | 2.10 | 35 | 15 | 0.97 | 0.98 |
| 4 | 0 | 1 | 2.52 | 2.54 | 78262 | 10846 | 1.37 | 1.16 |
| 5 | 0 | 53 | 1.90 | 2.11 | 69528 | 20765 | 1.09 | 1.01 |
| 6 | 17 | 0 | 2.47 | 1.98 | 179 | 65026 | 1.05 | 1.21 |

In all cases in which both EC and binding acid were present, normalized ROX values were $\geq 1.89$.

In all cases where binding acid was present, but extraction control was not added, normalized ROX values were $\leq 1.38$.

In all cases where extraction control was present, but binding acid was not added, normalized ROX values were $\leq 1.38$.

In all cases where the extraction control was added and CT target was successfully extracted, normalized ROX values were $\geq 1.89$.

In all cases where CT target was spiked, but not successfully extracted, the normalized ROX values were $\leq 1.38$.

The results are presented graphically in FIG. 2. The results demonstrate that the extraction control (EC) was successfully extracted from a sample and that it accurately identified instances where the extraction of specific target nucleic acid failed. Alternately, the above example can be performed with EC-26.3 (SEQUENCE ID NO. 2). Other extraction controls that conform to the design parameters of the present invention can also be used.

EXAMPLE 2

Figure 3A:
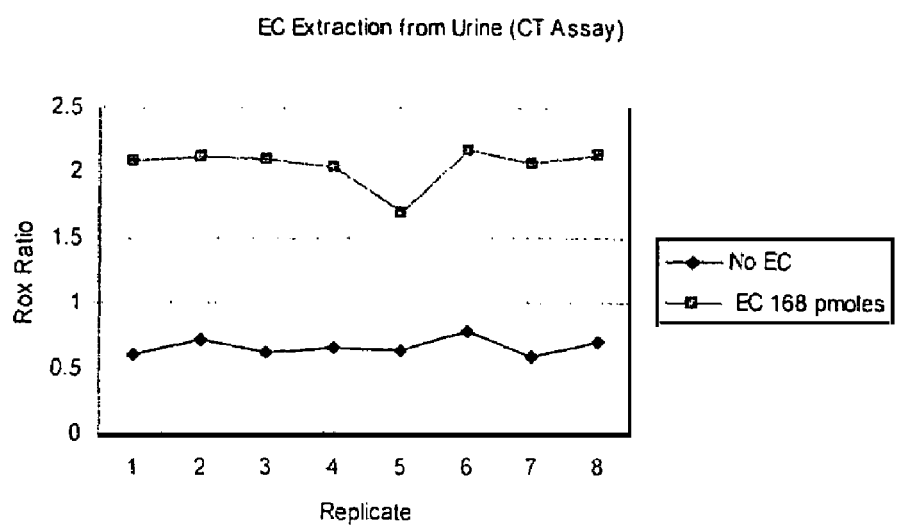
FIGS. 3a and 3b show the results of recovery of the extraction control (EC) from urine and vaginal specimens when used in conjunction with the BD ProbeTec™ ET Amplified CT (*Chlamydia trachomatis*) Assay in the absence of target DNA.
Figure 3B:
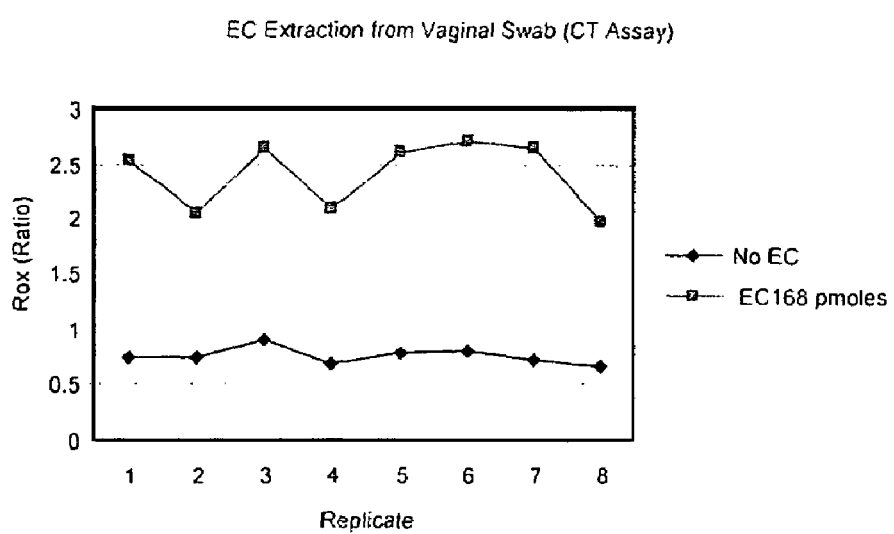
Figure 4A:
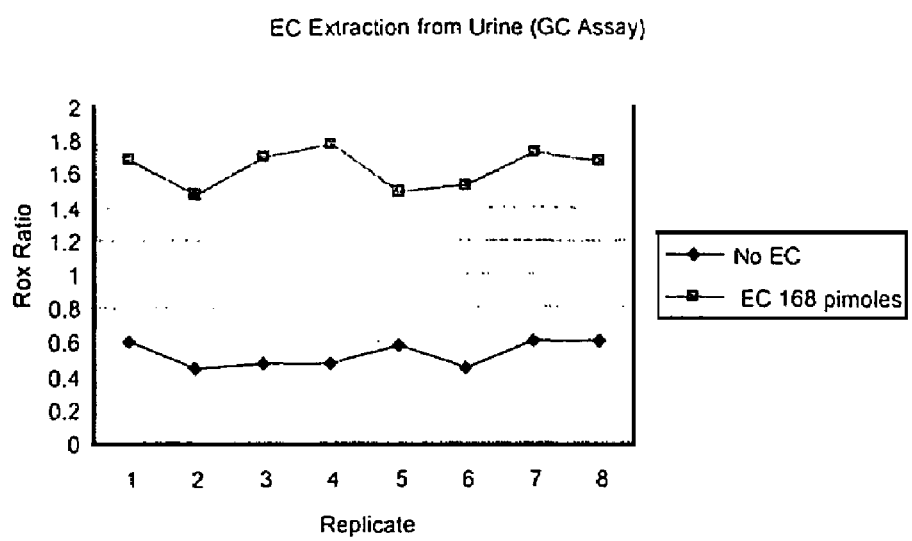
FIGS. 4a and 4b show the results of recovery of the extraction control (EC) from urine and vaginal specimens when used in conjunction with the BD ProbeTec™ ET Amplified GC (*Neisseria gonorrhoeae*) Assay in the absence of target DNA.
Figure 4B:
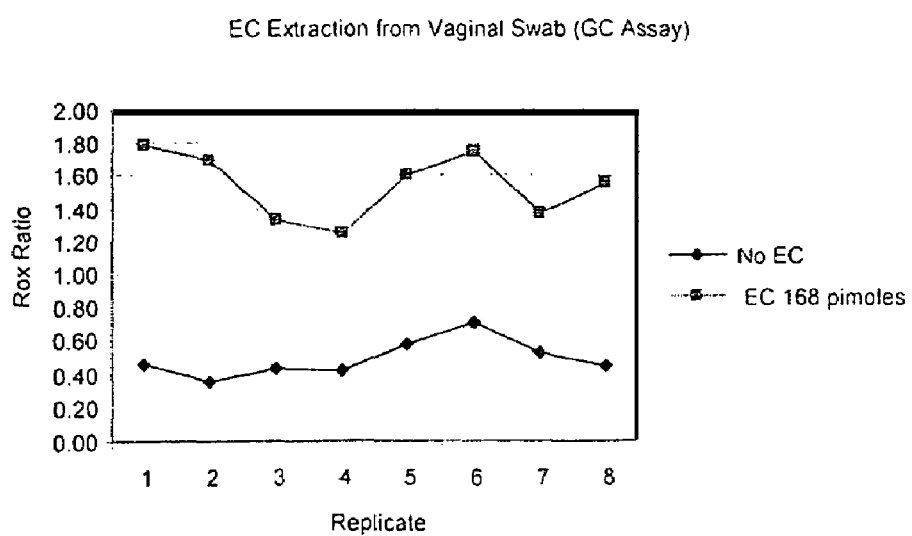
Figure 5:
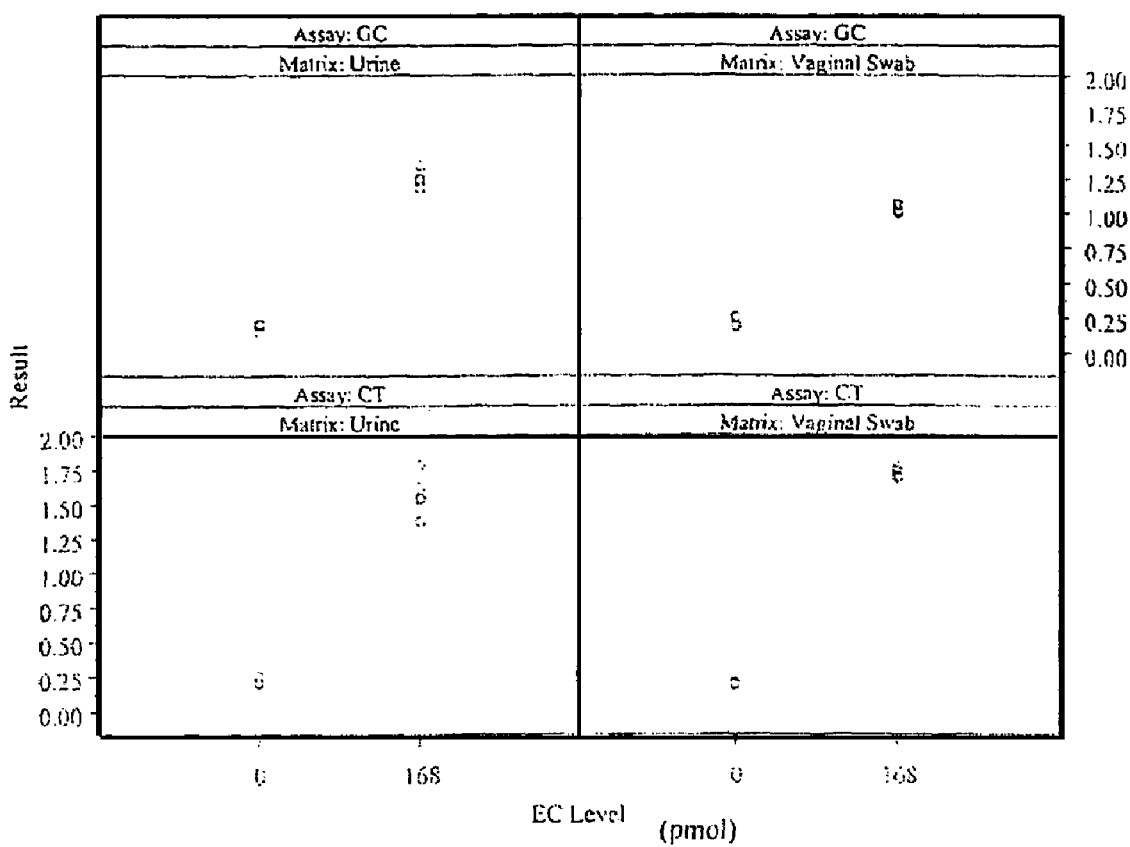
FIG. 5 shows the results of the recovery of the extraction control (EC) from two different biological matrices when used in either CT or GC assays.

To determine whether the EC could be extracted from different matrices, 168 pmol of the EC was spiked into pools of clinical urine and matrix from pressed vaginal swabs. Eight assay replicates were analyzed for each sample, including a negative control lacking EC. The results are presented in FIGS. 3, 4, and 5 for comparison.

EXAMPLE 3

Figure 6A:
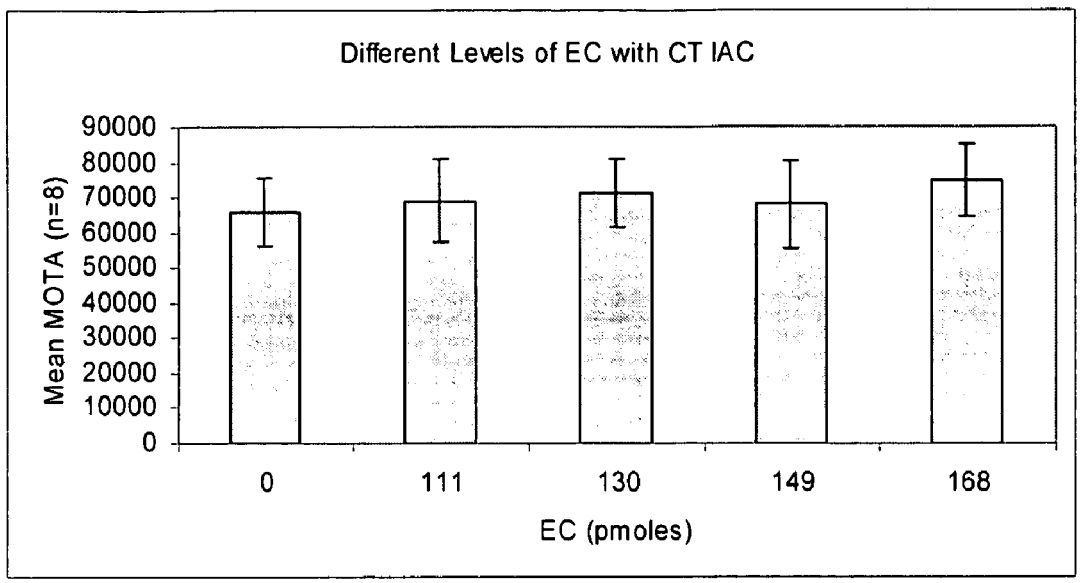
FIGS. 6a and 6b are graphs of the effects of different levels of the extraction control (EC) on amplification and detection of an internal amplification control (IAC) used in strand displacement amplification (SDA) assays for *Chlamydia trachomatis* (CT) and *Neisseria gonorrhoeae* (GC). The results show that the extraction control does not interfere with subsesquent analysis of the extracted nucleic acid by amplification and fluorescence-based detection.
Figure 6B:
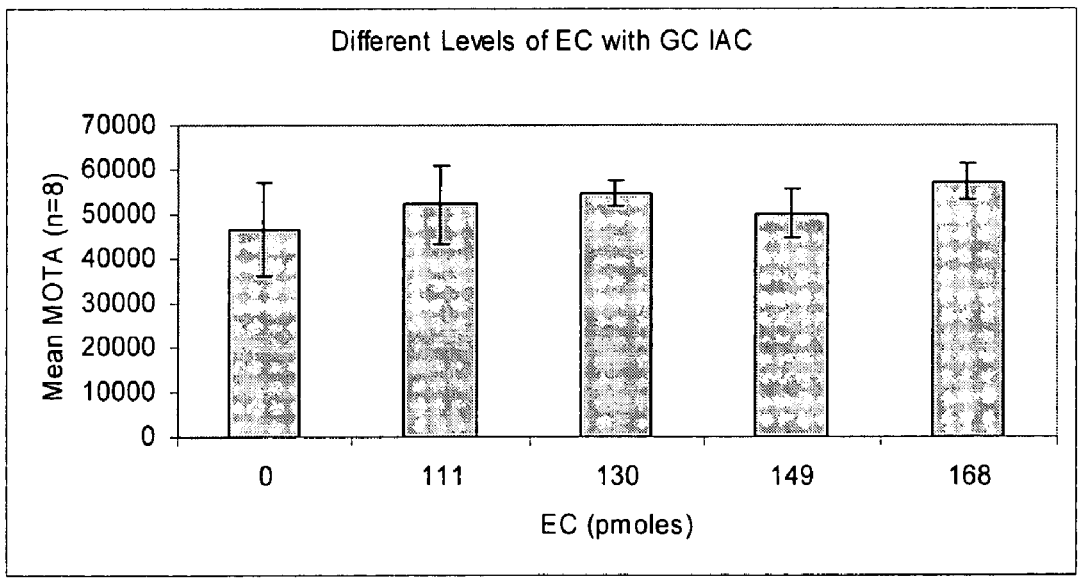
Figure 7:
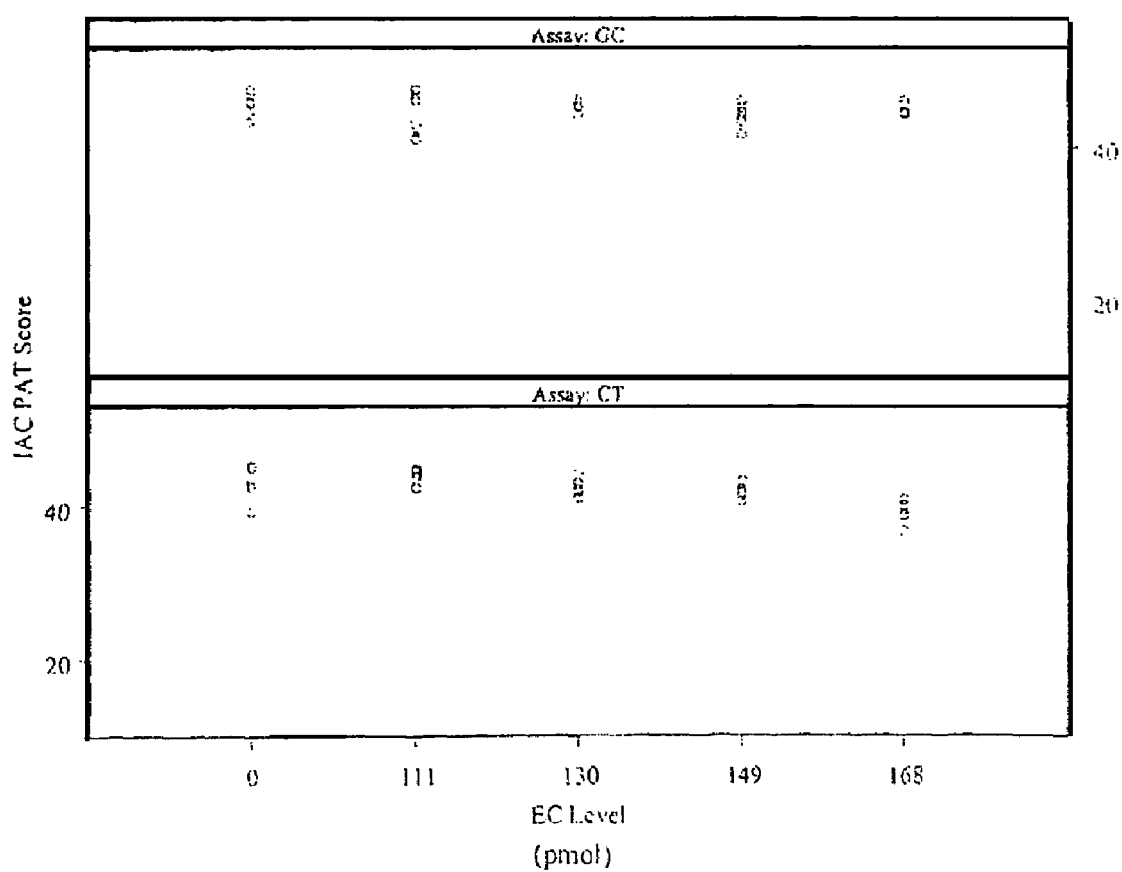
FIG. 7 shows the effect of an extraction control (EC) on the downstream detection of internal amplification controls (IACs) that are employed in SDA-based assays for *Chlamydia trachomatis* (CT) and *Neisseria gonorrhoeae* (GC). The efficiency of amplification of the IAC is monitored using a passes-after-threshold (PAT) algorithm.

The effect of the extraction control (EC) on a separate internal amplification control (IAC) was assessed by adding different levels of the EC to a pool containing matrix from pressed vaginal swabs and extracting as described in Example 1. The resulting eluates were tested in strand displacement amplification assays for CT and GC which contained internal amplification controls. The results are presented in FIGS. 6 and 7, which show that the extraction control does not interfere with the subsequent amplification for the internal amplification controls. The internal amplification control is given a score in a passes-after-threshold (PAT) algorithm. The thresholds for the PAT algorithm are set by performing a Receiver Operator Characteristic curve analysis on the assay results obtained with positive and negative controls. A preliminary threshold is found, and applied to results obtained with spiked samples for verification.

EXAMPLE 4

A sequence-specific extraction is performed by modification of Example 1. In place of iron oxide particles, streptavidin-coated beads are used. The beads are mixed with two different biotinylated oligonucleotides, one of which is complementary to the target sequence, while the other is complementary to the extraction control sequence. The extraction control is labeled with rhodamine. Appropriate conditions for hybridization as are well known in the art are used in the extraction step. Variation in salt concentration, temperature, cosolvent, and detergent are used to vary the stringency of hybridization specificity. Following hybridization, the beads are washed under appropriate conditions to remove debris and non-hybridized material. The target nucleic acid and the extraction control are eluted under conditions of low salt, elevated temperature, or other method as known in the art. The rhodamine label of the extraction control is detected to verify the extraction process, and the level of recovered rhodamine is quantified to determine the efficiency of capture, washing, and elution. The results are expressed quantitatively or qualitatively.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

Alternate embodiments may not have been presented for a specific portion of the invention. Some alternate embodiments may result from a different combination of described portions, or other non-described alternate embodiments may be available for a portion. This is not to be considered a disclaimer of those alternate embodiments. It is recognized that many of those non-described embodiments are within the literal scope of the following claims, and others are equivalent.

What is claimed is:

1. A method of detecting, verifying, and/or calibrating the extraction of nucleic acid from a biological sample, the method comprising:
   a) obtaining a biological sample;
   b) combining one or more reference nucleic acids with the biological sample;
   c) extracting nucleic acid from the biological sample concurrently with and/or after step b to yield an extract; and
   d) detecting the presence of and/or quantifying the amount of reference nucleic acid in the extract;
   e) estimating the amount of non-reference nucleic acid present in the composition before the extraction step by
      i) quantifying the amount of total nucleic acid and the amount of reference nucleic acid in the extract of step c;
      ii) comparing the amount of reference nucleic acid in the extract of step c to the amount of reference nucleic acid combined with the biological sample in step a to calculate a ratio of extraction efficiency; and
      iii) subtracting the amount of reference nucleic acid in said extract from the amount of total nucleic in said extract to yield the amount of non-reference nucleic acid in said extract; and
      iv) dividing the amount of non-reference nucleic acid in the extract by the ratio of extraction efficiency,
wherein the reference nucleic acid is capable of being detected and/or quantified without an amplification step, and further wherein the reference nucleic acid is capable of being detected without interference from material in the biological sample.

2. The method of claim 1, wherein the biological sample is body fluid from a human selected from the group consisting of urine, saliva, whole blood, plasma, lymph fluid, semen, vaginal fluid, sweat, tears, and mixtures thereof.

3. The method of claim 1, wherein quantifying the amount of reference nucleic acid in the extract of step c comprises: amplifying the reference nucleic acid, quantifying the amount of amplified nucleic acid, and calculating the amount of reference nucleic acid in the extract by multiplying the amplified amount of reference nucleic acid by a ratio of amplification efficiency.

4. The method of claim 1, wherein the reference nucleic acid comprises RNA or DNA labeled with a detectable moiety selected from the group consisting of a chromophore, a fluorophor, a radiolabel, or is enzyme, or is detectable by hybridization.

5. The method of claim 4, wherein the reference nucleic acid has a 3' end modified to essentially prohibit enzymatic chain extension.

6. The method of claim 4, wherein the reference nucleic acid contains a nucleic acid sequence selected from a known intron sequence and/or is capable of forming an internal hairpin structure.

7. The method of claim 1, wherein step c comprises either
   c1) reversibly binding nucleic acid to a solid support, washing the solid support to remove molecules that are bound less tightly than nucleic acid, and releasing nucleic acid from the solid support; or
   c2) irreversibly binding nucleic acid to a solid support, and washing the solid support to remove molecules that are bound less tightly than nucleic acid.

8. The method of claim 1, wherein the biological sample contains nucleic acid obtained from an organism selected from the group consisting of *Chlamydia trachomatis* and *Neisseria gonorrhoeae*.

9. The method of claim 1, wherein the reference nucleic acid comprises a set of two or more different nucleic acids that can be detected and/or quantified independently of each other.

10. A method of detecting, verifying, and/or calibrating the extraction of nucleic acid from a biological sample, the method comprising:
    a) obtaining a biological sample;
    b) combining one or more reference nucleic acids with the biological sample;
    c) extracting nucleic acid from the biological sample concurrently with and/or after step b to yield an extract; and
    d) detecting the presence of and/or quantifying the amount of reference nucleic acid in the extract;

wherein the reference nucleic acid is capable of being detected and/or quantified without an amplification step, and further wherein the reference nucleic acid is capable of being detected without interference from material in the biological sample;
and further wherein the reference nucleic acid is SEQ. ID NO. 1 and/or SEQ. ID NO. 2.

11. A method of analyzing a biological sample comprising:
    a) obtaining a biological sample;
    b) combining one or more reference nucleic acids with the biological sample, wherein the reference nucleic acid is capable of being detected and/or quantified without an amplification step, and further wherein the reference nucleic acid is capable of being detected without interference from material in the biological sample;
    c) extracting nucleic acid from the biological sample concurrently with and/or after step b to yield an extract; and
    d) detecting the presence of and/or quantifying the amount of reference nucleic acid in the extract;
    e) calculating an extraction efficiency ratio by dividing the amount of extracted reference nucleic acid by the amount of original reference nucleic acid, wherein the extraction efficiency ratio is greater than zero; and
    f) assaying the extract for a target nucleic acid.

12. The method of claim 11, wherein the target nucleic acid is indicative of a disease state or condition.

13. The method of claim 11, wherein the target nucleic acid is from an organism selected from the group consisting of *Chlamydia trachomatis* and *Neisseria gonorrhoeae*, and wherein the assay in step f is based on the presence of a primary structure selected from the group consisting of a structural gene, open reading frame, intron, exon, mRNA, cDNA or oligonucleotide sequence, and further wherein the reference nucleic acid is a truncated version of the target nucleic acid and contains about 50% or more of said primary structure.

14. The method of claim 11, wherein the reference nucleic acid is SEQ. ID NO. 1 and/or SEQ. ID NO. 2.

15. A packaged array for extracting nucleic acid from multiple biological samples, wherein the packaged array comprises:
    a) a set of first vessels containing reference nucleic acid, wherein the reference nucleic acid is capable of being detected and/or quantified without interference from target nucleic acid, and further wherein the detection and/or quantification is through a labeled moiety attached to the reference nucleic acid or through hybridization without amplification of the reference nucleic acid to a labeled species; and
    b) a means for extracting nucleic acid; and
    c) optionally a set of second vessels for independent placement of multiple biological samples that allows for transfer of material between the first vessels and the second vessels wherein the reference nucleic acid is SEQ. ID NO. 1 and/or SEQ. ID NO. 2.

16. The packaged array of claim 15, wherein the reference nucleic acid is in a dry form suitable for combination with a biological sample and subsequent extraction.

17. The packaged array of claim 15, further comprising aliquots of a solid support having an affinity for nucleic acid located in the first vessels with the reference nucleic acid or in the optional second set of vessels for placement of multiple biological samples.

18. The packaged array of claim 15, wherein the multiple biological samples are to be tested for the presence of one or more nucleic acids obtained from an organism selected from the group consisting of *Chlamydia trachomatis* and *Neisseria gonorrhoeae*.

* * * * *

SEQUENCE LISTING

```
<160> NUMBER OF SEQ ID NOS: 2

<210> SEQ ID NO 1
<211> LENGTH: 26
<212> TYPE: DNA
<213> ORGANISM: artificial sequence
<220> FEATURE:
<221> NAME/KEY: misc_feature
<222> LOCATION: (1)..(1)
<223> OTHER INFORMATION: Rhodamine (ROX) attached to the 5' end of the
      sequence (ie to residue 1).
<220> FEATURE:
<223> OTHER INFORMATION: This is a synthetic construct.

<400> SEQUENCE: 1
ttcatgcgag aggagatggc attaag                                              26

<210> SEQ ID NO 2
<211> LENGTH: 26
<212> TYPE: DNA
<213> ORGANISM: artificial sequence
<220> FEATURE:
<221> NAME/KEY: misc_feature
<222> LOCATION: (1)..(1)
<223> OTHER INFORMATION: Rhodamine (ROX) attached at the 5' end of the
      sequence (ie to residue 1).
<220> FEATURE:
<223> OTHER INFORMATION: This is a synthetic construct.

<400> SEQUENCE: 2
tctatgattg ttattatttc ttatat                                              26
```